United States Patent [19]

Narita et al.

[11] Patent Number: 5,097,040

[45] Date of Patent: * Mar. 17, 1992

[54] BENZOTRIAZOLE DERIVATIVES AND REAGENTS FOR DETERMINING CARBOXYLIC ACIDS THEREOF

[75] Inventors: Shigeru Narita; Takayasu Kitagawa, both of Osaka, Japan

[73] Assignee: Shionogi & Co., Ltd., Osaka, Japan

[*] Notice: The portion of the term of this patent subsequent to Mar. 26, 2008 has been disclaimed.

[21] Appl. No.: 613,688

[22] PCT Filed: May 25, 1989

[86] PCT No.: PCT/JP89/00519

§ 371 Date: Nov. 20, 1990

§ 102(e) Date: Nov. 20, 1990

[87] PCT Pub. No.: WO89/12045

PCT Pub. Date: Dec. 14, 1989

[30] Foreign Application Priority Data

Jun. 3, 1988 [JP] Japan .................. 63-138039

[51] Int. Cl.$^5$ .......................................... C07D 249/20
[52] U.S. Cl. .................................. 548/259; 548/257; 436/815
[58] Field of Search ............... 548/257, 259, 260

[56] References Cited

U.S. PATENT DOCUMENTS 4,937,348 6/1990 Kubota .................. 548/260
5,003,076 3/1991 Narita et al. ........... 548/259

FOREIGN PATENT DOCUMENTS 0363964 4/1990 European Pat. Off. ......... 548/260

89/12044 12/1989 PCT Int'l Appl. ........... 548/257
89/12045 12/1989 PCT Int'l Appl. ........... 548/257

OTHER PUBLICATIONS

Narita et al., Analytical Sciences, vol. 5 pp. 31-34; 361-362; vol. 37, pp. 831-833 (1989).

Primary Examiner—Donald G. Daus
Attorney, Agent, or Firm—Wenderoth, Lind & Ponack

[57] ABSTRACT

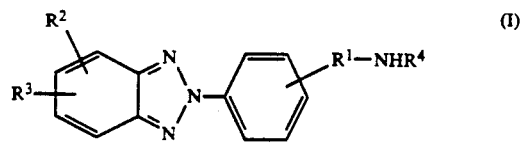

The invention provides compounds represented by formula (I) and their salts, wherein $R^1$ represents $C_1$–$C_5$ alkylene, $R^2$ and $R^3$, which may be the same or different, each represents hydrogen, $C_1$–$C_5$ alkyl, $C_1$–$C_5$ alkyloxy, amino, mono- or di-$C_1$–$C_5$ alkylamino (provided that $R^2$ and $R^3$ do not represent hydrogen at the same time) or, when taken together, represent $C_1$–$C_5$ alkylenedioxy, and $R^4$ represents hydrogen or $C_1$–$C_5$ alkyl. Since the compounds react with a carboxylic acid in a short time at room temperature in the presence of a condensing agent to produce amides emitting strong fluorescence, they are useful as reagents for determining the presence of carboxylic acids rapidly with high sensitivity.

2 Claims, 1 Drawing Sheet

BENZOTRIAZOLE DERIVATIVES AND REAGENTS FOR DETERMINING CARBOXYLIC ACIDS THEREOF

FIELD OF THE INVENTION

Carboxylic acids exist widely in the living body as the metabolites of carbohydrates, lipides, and proteins, and each acid plays important parts. This invention relates to compounds suitable for microanalysis of these carboxylic acids and to fluorescence labeling reagents thereof.

BACKGROUND OF THE INVENTION

Figure 1:
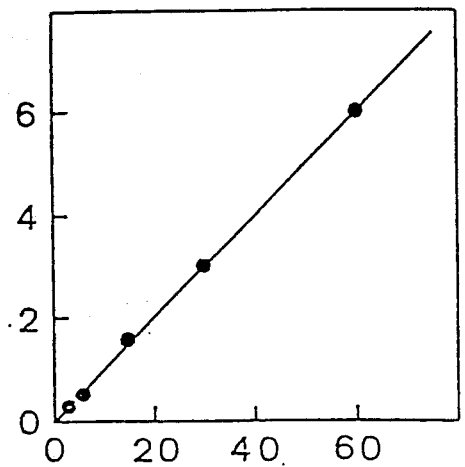
FIG. 1 illustrates the relationship between the concentration of flufenamic acid and the peak area of the chromatogram, where the ordinate shows the peak area ($\times 10^4$) and the abscissa the concentration of flufenamic acid (ng/500 ul).

Recently, attention has been paid to prostaglandins with a wide variety of physiological activities, bile acids metabolized from cholesterol and oxy acids, keto acids, etc which are thought important for the diagnosis or the treatment of congenital dysbolism, so it is hoped to develop a method for quantitative detection of them with symplicity, rapidity, and high sensitivity.

Nimura et al disclose 9-anthryldiazomethane (N. Nimura, T. Kinoshita: Anal. Lett., 13, 191 <1980>). 9-Anthryldiazomethane is advantageous in its reactivity with carboxylic acids at room temperature, but often causes problems in the course of detection because of its unstability.

Tsuchiya et al disclose the method for fluorescence detection of 7-hydroxy-4-hydroxymethylcoumarin, prepared by labeling carboxylic acids with 7-acetoxy-4-bromomethylcoumarin (ABMC), separating the same by reversed phase HPLC followed by alkaline hydrolysis (H. Tsuchiya et al: J. Chromatogr., 234, 121 (1982)). This method has a merit that the detection limit is high (several ten fmol) without the influence of the solvent in the mobile phase, but some demerits in that it needs complicated procedures such as heating in the case of the reaction of carboxylic acids with ABMC, and alkaline hydrolysis after separation.

DISCLOSURE OF THE INVENTION

In view of the circumstances above, the present inventors have tried to develop labeling reagents which are reactive under mild conditions and are highly sensitive but do not disturb the detection and have completed the present invention. The compounds, which the present invention provides are of the following formula:

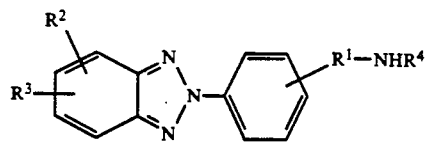

wherein $R^1$ means $C_1-C_5$ alkylene; $R^2$ and $R^3$ are each identical or different and are hydrogen, $C_1-C_5$ alkyl, $C_1-C_5$ alkyloxy, amino, or mono- or di-$C_1-C_5$ alkylamino, except that $R^2$ and $R^3$ are not both hydrogen at the same time, or form together $C_1-C_5$ alkylendioxy; and $R^4$ means hydrogen or $C_1-C_5$ alkyl, or a salt thereof (hereafter referred to simply as the compounds of this invention). The compounds react with carboxylic acid quickly at room temperature in the presence of a condensing reagent. The reaction products are amides having strong fluorescence and excessive reagents can be eliminated easily. Thus, the compounds of this invention make the detection of carboxylic acids, simple, rapid, very sensitive, and therefore they are useful.

The compounds of this invention react with carboxylic acids in an aprotic solvent in the presence of a condensing reagent and a base or an acid-scavenger in place of the base, within about 30 minutes at room temperature. Thereby corresponding amides showing strong fluorescence are formed. Besides, excessive reagents can be removed easily from the reaction mixture by passing the reaction solution through a silicagel column for the pretreatment. The compounds of this invention react with a wide variety of carboxylic acids, regardless of whether they are aromatic or aliphatic ones. It is desirable that $R^2$ and $R^3$ have higher electron-donating property, since such property gives high fluorescence intensity to the resulting compound.

The compound of this invention can be prepared easily by known reactions in the field of organic chemistry. For example, as shown below, substituted aniline (a) is subjected to the known diazo coupling reaction with diazo compound (b) having an aminoalkyl group protected by a suitable protective group (Step 1), then to oxidative ring-closing reaction (Step 2), followed by deprotection (Step 3), to give the compound (I) of this invention.

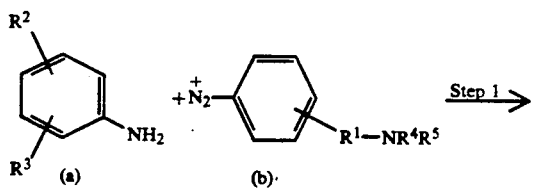

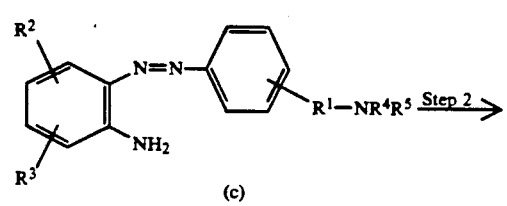

-continued

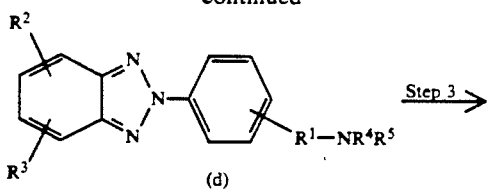

The compound (I) of this invention.

In the reaction scheme, $R^1$, $R^2$, $R^3$, and $R^4$ each has the same meaning as defined above, $R^5$ means a protective group.

The process above is explained below step by step.

Step 1

The reaction is usually carried out in an aqueous solution at a temperature from ice-cooling to 15° C. Aniline derivative corresponding to the diazo compound (b) is dissolved or suspended in an inorganic acid, which is then reacted with nitrous acids such as sodium nitrite to obtain the highly reactive diazo compound (b). Sulfamic acid or urea is added thereto to remove excessive nitrous acids.

Next, the substituted aniline compound (a) is added thereto, whereby it is easily coupled with the diazo compound (b) to give the compound (c). The reaction is completed in several minutes to several hours.

Step 2

The azo group of the compound (c) easily forms an oxidative ring closure with the adjacent amine to give the triazole compound (d). The reaction is completed in several minutes to several ten hours at room temperature or under heating, if carried out in a water-containing organic solvent in the presence of a copper-ammonia complex.

Step 3

The compound (d) is subjected to hydrolysis in a water-containing organic solvent in the presence of an acid or a base to give the compound (I) of this invention. The reaction is completed in several minutes to several days at room temperature or under heating.

In the invention, $C_1-C_5$ alkylene means a straight chain $C_1-C_5$ alkylene including methylene, ethylene, propylene, butylene, and pentylene, especially methylene or ethylene is preferable. $C_1-C_5$ alkyl means a straight or branched chain $C_1-C_5$ alkyl, including methyl, ethyl, n-propyl, isopropyl, n-butyl, sec-butyl, tert-butyl, n-pentyl, isopentyl, neopentyl, and tert-pentyl, etc.

As for the protecting group, all the known protecting groups for amine can be used. Among others, those stable for acids are preferable, for example, acetyl, trifluoroacetyl, and benzoyl, etc.

The representative examples of the compounds of this invention are listed below, which do not limit the scope of the invention.

(1) 2-(p-aminomethylphenyl)-N,N-dimethyl-2H-benzotriazolyl-5-amine,
(2) 2-[p-(2-aminoethyl)phenyl]-N,N-dimethyl-2H-benzotriazolyl-5-amine dihydrochloride,
(3) 2-(p-aminomethylphenyl)-2H-benzotriazolyl-5amine,
(4) p-(5,6-dimethoxy-2H-benzotriazol-2-yl)benzylamine,
(5) 2-[p-(5,6-methylenedioxy-2H-benzotriazol-2-yl)]phenethylamine,
(6) 4-[m-(5-propoxy-2H-benzotriazol-2-yl)phenyl]-butylamine,
(7) 4-butoxy-2-[(3-m-methylaminopropyl)phenyl]-2H-benzotriazolyl-5-amine,
(8) N-butyl-5-[o-(5-ethoxy-7-butyl-2H-benzotriazol-2-yl)phenyl]pentylamine,
(9) N-isopropyl-2-[m-(5,6-ethylenedioxy-2H-benzotriazol-2-yl)]phenethylamine, and
(10) 2-(o-aminomethylphenyl)-N,N-dimethyl-2H-benzotriazolylene-5, 6-diamine.

This invention is further explained in the following Examples and Experiments, which are not intended to limit the scope of this invention.

EXAMPLE

The compounds 1-5 of this invention were prepared as shown in the following Examples 1-5. Physical constants on each compound are shown on table 1.

EXAMPLE 1

Preparation of 2-(p-aminomethylphenyl)-N,N-dimethyl-2H-benzotriazolyl-5-amine (1)

To a solution of N-(p-aminobenzyl)acetamide (6.6 g) dissolved in 100 ml of 10% hydrochloric acid was added 10% sodium nitrite (30 ml), while being stirred under ice-cooling. Fifteen minutes later, 10% ammonium sulfamate (50 ml) was added thereto, and the mixture was stirred for 15 minutes. The reaction mixture was adjusted to about pH 5 with sodium acetate, added with N,N-dimethyl-m-phenylenediamine dihydrochloride (8.4 g), and the resulting mixture was stirred for 4 hours.

The reaction mixture was adjusted to about pH 9 with 1N sodium hydroxide, filtered to collect precipitates, which were then washed well with water. They were recrystallized from dimethylformamide/methanol to give the pure azo compound as red plates, m.p. 138°-139° C.

To a solution of the resulting azo compound (8.7 g) dissolved in pyridine (100 ml) was added an ammoniacal cupric sulfate solution which was prepared by dissolving cupric sulfate pentahydrate in 150 ml of 14% aqueous ammonia, then the mixture was refluxed for 4 hours. After completion of the reaction, the mixture was cooled and extracted with ethyl acetate. The ethyl acetate layer was dried over anhydrous sodium sulfate and evaporated to leave a residue, which was recrystallized from aqueous ethanol to give the objective compound (1) as acetate, yellow needles, m.p. 196°-197° C. To a solution of the acetate (7 g) dissolved in ethanol (200 ml) was added 10% hydrochloric acid (50 ml), then the mixture was refluxed for 5 days. After completion of the reaction, the reaction mixture was concentrated to about 50 ml (total volume), and filtered. The filtrate was neutralized with sodium bicarbonate to leave precipitates, which were collected by filtration, washed well with water, and recrystallized from methanol to give the objective compound (1).

EXAMPLE 2

Preparation of 2-[p-(2-aminoethyl)phenyl]-N,N-dimethyl-2H-benzotriazolyl-5-amine dihydrochloride (2)

The reaction was performed according to the same manner as in Example 1 except that N-(p-aminophenethyl)-2,2,2-trifluoroacetamide hydrochloride (8.1 g) was used in place of N-(p-aminobenzyl)acetamide. The extract which resulted from an oxidative ring closure reaction with an ammoniacal cupric sulfate solution was dissolved, without recrystallization, in ethanol (50 ml), combined with 5N aqueous solution of sodium hydroxide (20 ml), and the mixture refluxed for 2 hours. After completion of the reaction, the mixture was combined with water (100 ml) and extracted with ethyl acetate. The ethyl acetate layer was evaporated under reduced pressure and the oily residue was dissolved in ethyl ether (20 ml). After filtration, the filtrate was added to an ethanolic solution of hydrochloric acid to give the objective compound (2).

EXAMPLE 3

Preparation of 2-(p-aminomethylphenyl)-2H-benzotriazolyl-5-amine (3)

The reaction was performed according to the same manner as in Example 1, except that m-phenylenediamine dihydrochloride (7.2 g) was used in place of N,N-dimethyl-m-phenylenediamine dihydrochloride, to give the objective compound (3).

EXAMPLE 4

Preparation of p-(5,6-dimethoxy-2H-benzotriazol-2-yl) benzylamine (4)

The reaction was performed according to the same manner as in Example 1, except that 3,4-dimethoxyaniline (6.4 g) was used in place of N,N-dimethyl-m-phenylenediamine dihydrochloride, to give the objective compound (4).

EXAMPLE 5

Preparation of 2-[p-(5,6-methylenedioxy-2H-benzotriazol-2-yl)]phenethylamine (5)

The reaction was performed according to the same manner as in Example 2, except that 3,4-methylenedioxyaniline (5.6 g) was used in place of N,N-dimethyl-m-phenylenediamine dihydrochloride. After the completion of hydrolysis, the reaction mixture was extracted with ethyl acetate, and the organic layer was evaporated under reduced pressure to leave a residue, which was recrystallized from methanol to give the objective compound (5).

TABLE 1

| No | Appearance IR (Nujol) | m.p. (°C.) | Molecular Formula | Elementary Analysis (Calcd./Found) C | H | N |
|---|---|---|---|---|---|---|
| 1 | yellow needles 3300, 3380 | 127–128 | $C_{15}H_{17}N_5$ | 67.39 67.45 | 6.41 6.37 | 26.20 26.15 |
| 2 | light red plates 2450, 2550 | 250–260 | $C_{16}H_{21}N_5Cl_2$ | 54.24 53.58 | 5.97 5.96 | 19.77 19.52 |
| 3 | yellow plates 3150, 3300, 3350, 3430 | 206–207 | $C_{13}H_{13}N_5$ | 65.25 65.27 | 5.48 5.51 | 29.27 29.18 |
| 4 | colorless needles 3300, 3350, 3480 | 155–156 | $C_{15}H_{16}N_4O_2 \cdot \frac{1}{2}H_2O$ | 61.42 61.54 | 5.84 5.83 | 19.10 19.05 |
| 5 | colorless needles 1713, 3230, | 145–147 | $C_{15}H_{14}N_4O_2 \cdot \frac{1}{2}H_2O$ | 62.82 62.66 | 5.10 5.21 | 19.54 19.55 |

EXPERIMENT

General Procedures for Analysis

In a 10 ml vial, 0.5 ml of an acetonitrile solution of a carboxylic acid compound is placed and acetonitrile solutions of 2-bromo-1-ethylpyridinium tetrafluoroborate (3.7 mM), 9-methyl-3, 4-dihydro-2H-pyurido[1,2-a]pyrimidin-2-one (2.7 mM), and the compound of this invention (3.7 mM), are added thereto by 50 µl each and the mixture stirred for about 10 seconds. This solution is allowed to stand at room temperature for about 30 minutes.

This solution (0.5 ml) is passed through a silicagel column for the pretreatment, with acetonitrile (1.5 ml) as an eluent. Acetonitrile is added to the eluent to make the whole 2.5 ml, 20 µl of which is subjected to HPLC. Excitation wavelength and fluorescence wavelength on each reagent in acetonitrile are shown in Table 2.

EXPERIMENT 1

The Compound 1 of this Invention as Reagent

Acetonitrile solutions (0.5 ml each) containing 3, 6, 15, 30, or 60 ng of flufenamic acid were placed into 10 ml vials. To each vial were added acetonitrile solutions (50 µl each) of 2-bromo-1-ethylpyridinium tetrafluoroborate (3.7 mM), 9-methyl-3, 4-dihydoro-2H-pyrido[1,2-a]pyrimidin-2-one (2.7 mM), and the compound of this invention (3.7 mM), and the mixture were stirred for about 10 seconds. These were allowed to stand at room temperature for about 30 minutes.

Each of these solutions (0.5 ml) was passed through a Bond Elut column (silicagel) and eluted with acetonitrile (1.5 ml). The total amount of the eluate was made 2.5 ml with acetonitrile, the resulting solution (20 µl) was subjected to HPLC.

Conditions for Measurement

Figure 2:
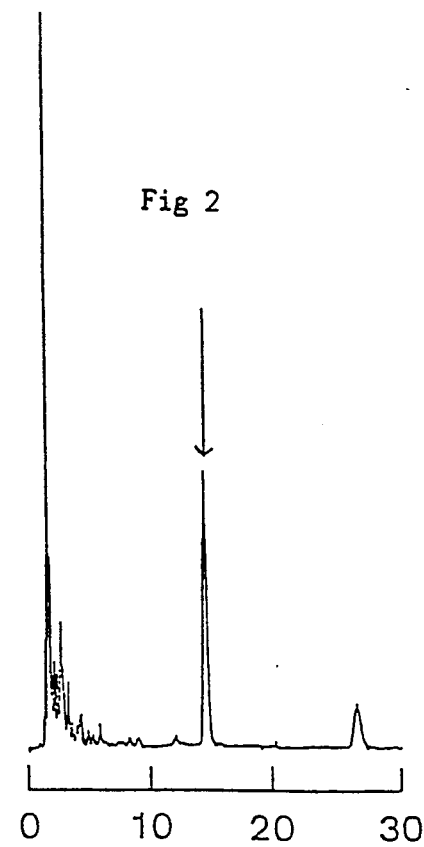
FIG. 2 is the chromatogram obtained in Experiment Example 1, where the abscissa shows retention time (minute) and the peak indicated by the arrow corresponds to flufenamic acid (about 0.2 ng).

Apparatus: Shimadzu LC-4A Pump (Shimadzu) Shimadzu RF-535 Fuluorescence HPLC Monitor (same as above)
Column: Novapack $C_{18}$(3.9×150 mm; Waters)
Guard Column: Nucleosil $5C_{18}$(4.0×30 mm; Nagel)
Mobile Phase: acetonitile/water—2/1
Flow Rate: 1.2 ml/minute
Wavelength: 395 nm for excitation, 510 nm for fluorescence emission Results The relationship between the concentration of flufenamic acid and the peak area of the chromatogram as obtained in the experiment above is shown in FIG. 1. The chromatogram is shown in FIG. 2.

EXPERIMENT 2

The Compound 5 of this Invention as Reagent

The experiment was performed in the same way as Example 1, except that the compound 5 of this invention was used as a reagent to acetonitrile solutions (0.5 ml each) containing 0.6, 3, 6, 15, 30, or 60 ng of ibuprofen.

Conditions for Measurement

Apparatus: same as Example 1
Column: Nucleosil $5C_{18}$(4.6×150 mm; Nagel)
Guard Column: same as Example 1
Mobile Phase: acetonitrile/water=5/3

Flow Rate: 1.0 ml/minute
Wavelength: 333 nm for excitation, 375 nm for fluorescence emission

Results

Figure 3:
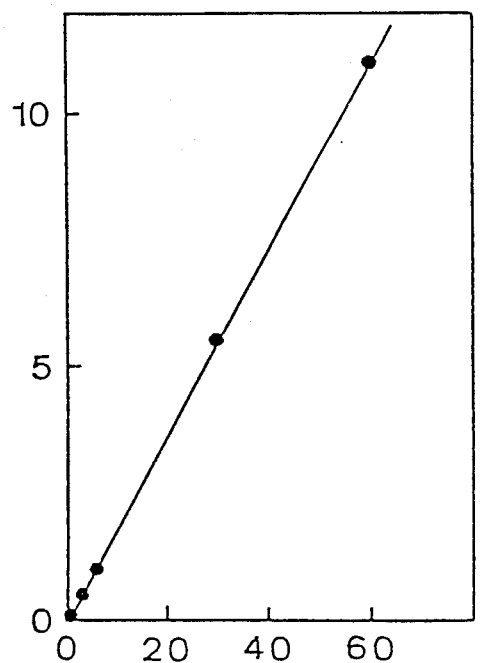
FIG. 3 illustrates the relationship between the concentration of ibuprofen and the peak area ($\times 10^6$) of the chromatogram, where the ordinate shows the peak area ($\times 10^6$) and the abscissa the concentration of ibuprofen.
Figure 4:
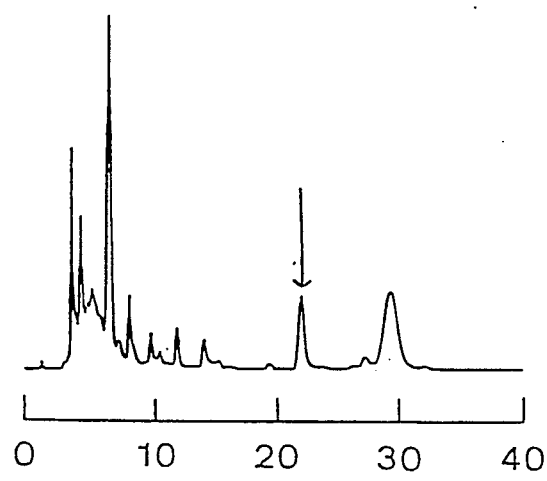
FIG. 4 is the chromatogram obtained in Experiment Example 2, where the abscissa shows retention time (minute) and the peak indicated by the arrow corresponds to ibuprofen (about 0.02 ng).

The relationship between the concentration of ibuprofen and the peak area of the chromatogram as obtained in the experiment above is shown in FIG. 3. The chromatogram is shown in FIG. 4.

EXPERIMENT 3

Table 2 shows both excitation and fluorescence wavelength of amide compounds in acetonitrile, which are the reactants of the compounds (1)–(5) of this invention with benzoic acid. The data of detection limit for each amide compound by HPLC is also shown.

TABLE 2

| No | Excitation Wavelength (nm) | Fluorescence Wavelength (nm) | Detection Limit (fmol) |
| --- | --- | --- | --- |
| 1 | 390 | 488 | 15 |
| 2 | 384 | 486 | 15 |
| 3 | 366 | 456 | 6 |
| 4 | 333 | 370 | 0.5 |
| 5 | 333 | 372 | 0.5 |

We claim:

1. A compound of the formula:

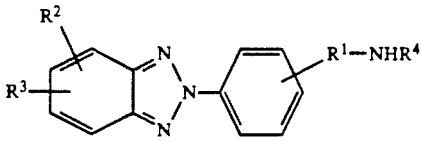

wherein $R^1$ is $C_1$-$C_5$ alkylene; $R^2$ and $R^3$ are each identical or different and are hydrogen, $C_1$-$C_5$ alkyl, $C_1$-$C_5$ alkyloxy, amino, or mono- or di-$C_1$-$C_5$ alkylamino, except that $R^2$ and $R^3$ are not both hydrogen at the same time, $R^2$ and $R^3$ taken together form $C_1$-$C_5$ alkylenedioxy; and $R^4$ is hydrogen or $C_1$-$C_5$ alkyl, or a salt thereof soluble in aprotic solvent.

2. A reagent for determining the presence of a carboxylic acid, comprising a compound of the formula:

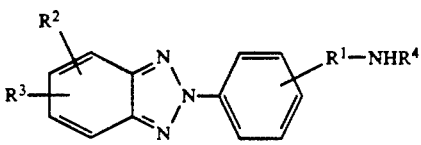

wherein $R^1$ is $C_1$-$C_5$ alkylene; $R^2$ and $R^3$ are each identical or different and are hydrogen, $C_1$-$C_5$ alkyl, $C_1$-$C_5$ alkyloxy, amino or mono- or di-$C_1$-$C_5$ alkylamino, except that $R^2$ and $R^3$ are not both hydrogen at the same time, or $R^1$ and $R^2$ taken together form $C_1$-$C_5$ alkylenedioxy; and $R^4$ is hydrogen or $C_1$-$C_5$ alkyl, or a salt thereof soluble in aprotic solvent.

* * * * *